United States Patent
Fleischer et al.

(10) Patent No.: US 7,707,869 B2
(45) Date of Patent: May 4, 2010

(54) FET-BASED GAS SENSOR

(75) Inventors: Maximilian Fleischer, Höhenkirchen (DE); Hans Meixner, Haar (DE); Elfriede Simon, München (DE); Uwe Lampe, Buxtehude (DE); Roland Pohle, Herdweg (DE)

(73) Assignee: Micronas GmbH, Freiburg (DE)

( * ) Notice: Subject to any disclaimer, the term of this patent is extended or adjusted under 35 U.S.C. 154(b) by 450 days.

(21) Appl. No.: 11/587,172

(22) PCT Filed: Apr. 21, 2005

(86) PCT No.: PCT/EP2005/004278
§ 371 (c)(1),
(2), (4) Date: Feb. 15, 2007

(87) PCT Pub. No.: WO2005/103666
PCT Pub. Date: Nov. 3, 2005

(65) Prior Publication Data
US 2007/0220954 A1      Sep. 27, 2007

(30) Foreign Application Priority Data
Apr. 22, 2004    (DE) ................ 10 2004 019 641

(51) Int. Cl.
*G01N 33/00* (2006.01)
*B01L 5/00* (2006.01)
(52) U.S. Cl. .......... 73/31.05; 73/23.31; 73/31.06
(58) Field of Classification Search .......... None
See application file for complete search history.

(56) References Cited

U.S. PATENT DOCUMENTS

| | | | |
|---|---|---|---|
| 3,663,870 A | 5/1972 | Tsutsumi et al. | |
| 4,023,549 A | 5/1977 | Hewitt | |
| 4,151,060 A | 4/1979 | Isenberg | |
| 4,354,308 A | 10/1982 | Shimada et al. | |
| 4,633,704 A | 1/1987 | Tantram et al. | |
| 4,638,346 A | 1/1987 | Inami et al. | |
| 4,792,433 A | 12/1988 | Katsura et al. | |
| 5,635,628 A | 6/1997 | Fleischer et al. | |

(Continued)

FOREIGN PATENT DOCUMENTS

DE     2947050     5/1981

(Continued)

OTHER PUBLICATIONS

Gergintschew et al., "The capacitively controlled field effect transistor (CCFET) as a new low power gas sensor," Sensors and Actuators B: Chemical, Elsevier Sequoia, vol. 36, No. 1, Oct. 1996, pp. 285-289.

(Continued)

*Primary Examiner*—Daniel S Larkin
(74) *Attorney, Agent, or Firm*—O'Shea Getz P.C.

(57) ABSTRACT

An operating method is disclosed for the selective detection of a target gas in a gas mixture to be measured by a field effect transistor with a gas-sensitive layer disposed on a carrier substrate, wherein the gas mixture to be measured is prepared by an electrochemical element such that the measured gas mixture includes minimal amounts of interfering gases that interfere with the measurement of the target gas, and/or at least one target gas is activated such that it is detected by the gas-sensitive layer.

28 Claims, 4 Drawing Sheets

U.S. PATENT DOCUMENTS

| | | | |
|---|---|---|---|
| 5,879,527 | A | 3/1999 | Kiesele et al. |
| 6,041,643 | A | 3/2000 | Stokes et al. |
| 6,454,834 | B1 | 9/2002 | Livingstone et al. |
| 6,566,894 | B2 | 5/2003 | Rump |
| 6,935,158 | B2 | 8/2005 | Serina et al. |
| 2002/0092974 | A1 | 7/2002 | Kouznetsov |
| 2004/0112764 | A1 | 6/2004 | Stokes et al. |
| 2004/0133116 | A1 | 7/2004 | Abraham-Fuchs et al. |
| 2005/0035808 | A1 | 2/2005 | Frerichs |

FOREIGN PATENT DOCUMENTS

| | | |
|---|---|---|
| DE | 4028062 | 3/1992 |
| DE | 4105598 | 8/1992 |
| DE | 4239319 | 4/1993 |
| DE | 4333875 | 4/1995 |
| DE | 19613274 | 10/1997 |
| DE | 197 08 770 | 8/1998 |
| DE | 10245947 | 4/2004 |
| EP | 0 947 829 | 10/1999 |
| EP | 0952447 | 10/1999 |
| EP | 1 059 528 | 12/2000 |
| EP | 1103809 | 5/2001 |
| EP | 1104884 | 6/2001 |
| EP | 1 176 418 | 1/2002 |
| JP | 01059049 | 3/1989 |
| JP | 3-131749 | 6/1991 |
| JP | 3-259736 | 11/1991 |
| WO | WO 94/23288 | 10/1994 |
| WO | WO 96/01992 | 1/1996 |
| WO | WO 98/41853 | 9/1998 |
| WO | WO 03/050526 | 6/2003 |

OTHER PUBLICATIONS

Fleischer et al., "Selective gas detection with high-temperature operated metal oxides using catalytic filters," Sensors and Actuators B, vol. 69, pp. 205-210, 2000.

Pohle et al., "Realization of a New Sensor Concept: Improved CCFET and SGFET Type Gas Sensors in Hybrid Flip-Chip Technology," Transducers, $12^{th}$ International Conference on Solid-State Sensors, Actuators and Microsystems, Jun. 2003, vol. 1, 9, pp. 135-138.

Peschke et al., "Optimization of Sputtered SnO2 Films as Gas-sensitive Layers for Suspended-gate FETs", Sensors and Actuators B, 1991, pp. 157-160, XP-002379749.

Lampe et al., "GasFET for the detection of reducing gases", Sensors and Actuators B 111-112, 2005, pp. 106-110.

Mizsei et al., "Simultaneous Response of Work Function and Resistivity of some SnO2-based Samples to H2 and H2S", Sensors and Actuators B, 4 (1991), pp. 163-168, XP-002379750.

Doll et al., "Gas detection with work function sensors", Proceedings of the SPIE, SPIE, Bellingham, VA, US, vol. 3539, Nov. 1998, pp. 96-105, XP-002329891.

Paris et al., "57.5: Low Drift Air-Gap CMOS-FET Gas Sensor," Proceedings of IEEE Sensors, vol. 1 of 2, Conf. 1, Jun. 12, 2002, pp. 421-425, 2002, XP010605129, ISBN: 0-7803-7454-1.

Burgmair et al., "Humidity and temperature compensation in work function gas sensor FETs," Sensors and Actuators B, Elsevier Sequoia S.A., Lausanne, CH, vol. 93, No. 1-3, pp. 271-275, 2003.

Burgmair et al., "Field effect transducers for work function gas measurements : device improvements and comparison of performance," Sensors and Actuators B, Elsevier Sequoia S.A., Lausanne, CH, vol. 95, No. 1-3, pp. 183-188, 2003.

Covington, et al. "Combined smart chemFET/resistive sensor array," Proceedings of the IEEE, vol. 2., pp. 1120-1123, 2003.

Doll et al., "Modular System Composed of Hybrid GasFET Modules," ITG-Technical Report 126: Sensors-Technology and Application, VDE Verlag, Berlin, Germany, 1994, pp. 465-470, XP-000874734.

M. Lehmann, "Nanometre Dimensions in Bio and Gas Sensor Technology", MST News, Mar. 2004, pp. 43-47, XP-002379751.

Abstract of DE 19534557 published Mar. 20, 1997, one page.

FET-BASED GAS SENSOR

PRIORITY INFORMATION

This patent application claims priority from International patent application PCT/EP2005/004278 filed Apr. 22, 2005 and German patent application 10 2004 019 641.9 filed Apr. 22, 2004, which are hereby incorporated by reference in their entirety.

BACKGROUND INFORMATION

Figure 6:
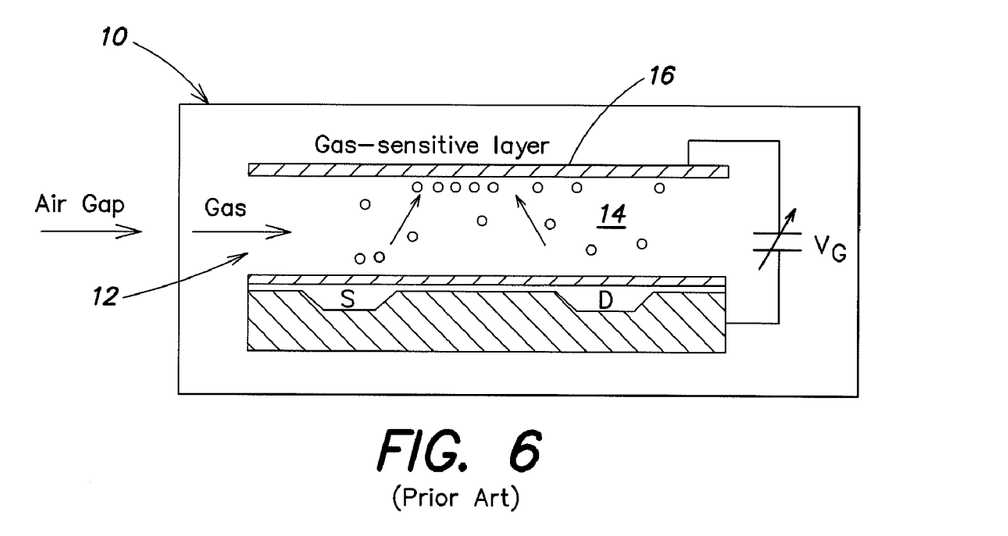
FIG. 6 is a schematic illustration of a prior art SGFET gas sensor.

Typically, a field effect transistor ("FET") gas sensor measures a change in a work function between a gas-sensitive material and a reference material. FIG. 6 is a schematic illustration of such a FET gas sensor 10. A gateless transistor 12 is capacitively coupled, through an air gap 14, to a gas-sensitive layer 16. The air gap 14 is configured as a gas inlet a few micrometers (μm) wide. The gas-sensitive layer 16 is adapted such that its surface potential changes upon contact with a gas within the air gap 14, and thus controls the transistor 12. The working temperatures of such a sensor are between ambient temperature and 150° C.

Figure 7:
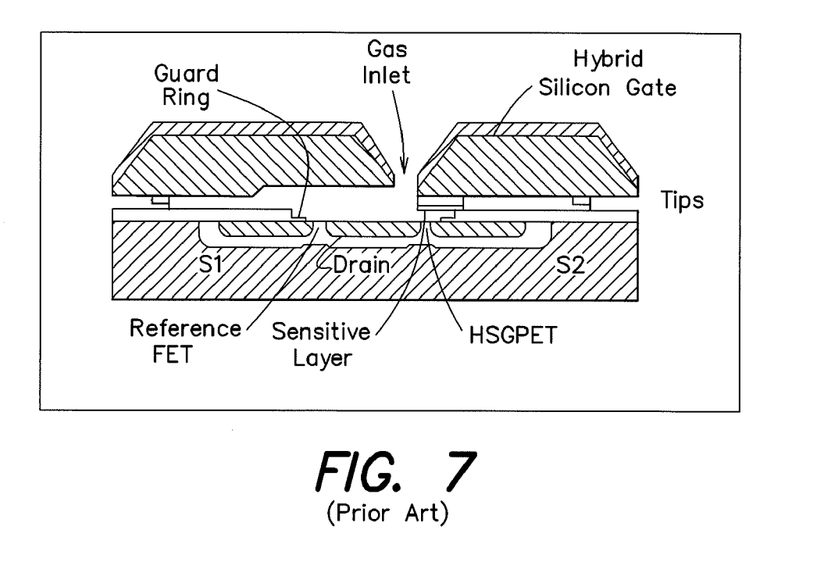
FIG. 7 is a diagrammatic illustration of a prior art SGFET gas sensor.

FIG. 7 is a diagrammatic illustration of a typical suspended gate FET ("SGFET") gas sensor. One example of such a SGFET gas sensor is disclosed in German Patent No. DE 4239319 C2, which is hereby incorporated by reference in its entirety.

Figure 8:
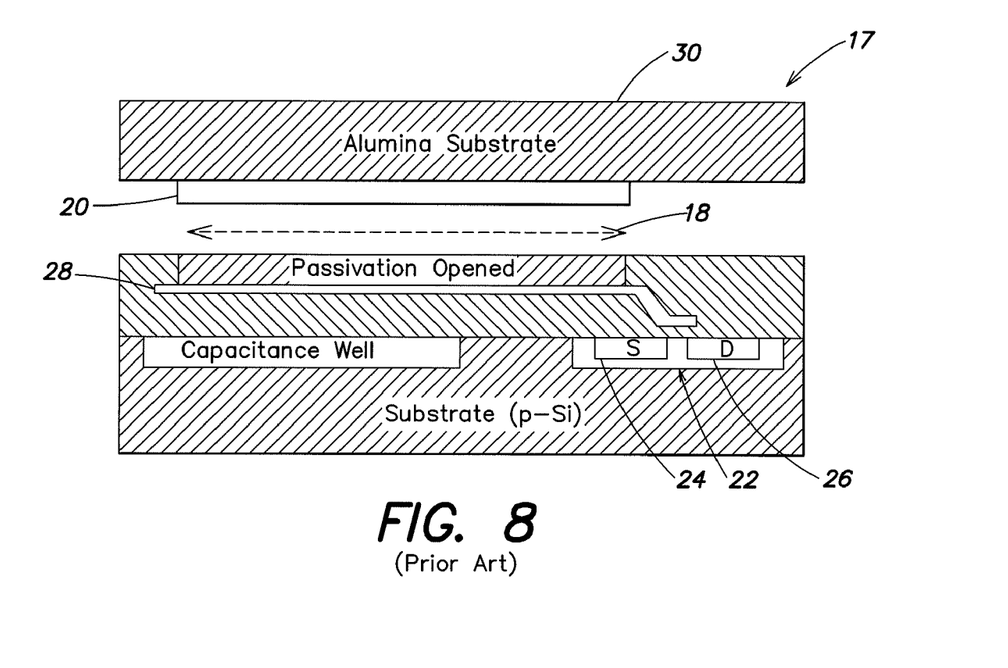
FIG. 8 is a diagrammatic illustration of a prior art CCFET gas sensor.

FIG. 8 is a diagrammatic illustration of a typical CCFET gas sensor 17. One example of such a CCFET gas sensor is disclosed in German Patent No. DE 4333875 C2, which is hereby incorporated by reference in its entirety. Referring again to FIG. 8, an air gap 18 and a gas-sensitive layer 20 are separated from a readout FET structure 22. The readout FET 22, which includes a source contact 24 and a drain contact 26, is controlled by an uncontacted gate 28. The uncontacted gate 98 and a gas-sensitive electrode 10 form a capacitor system.

Disadvantageously, the aforesaid gas sensors frequently measure reactions from interfering gases (i.e., non-target gases) within the air gap. "Undesired" signals from the interfering gases may be superimposed on a "desired" signal from a reaction of a target gas. As a result, this superposition may distort measurements of the target gas. In addition, these interfering gases may decrease the signal level of the target gas.

To increase accuracy of these FET gas sensors, several methods and systems have been developed to reduce the effects of interfering gases. For example, improvements may include (1) optimizing sensitive materials, (2) compensating for the interfering gases using a reference sensor, and (3) using a filter to suppress effects of the interfering gases.

First, sensitive materials in a FET gas sensor may be optimized. This may be accomplished by optimizing gas-sensitive materials and reference materials located on the transistor of the sensor to selectively reduce the influence of interfering gases.

Second, interfering gases may be compensated for by using a reference sensor. For example, a second sensor (i.e., a reference coating) sensitive to a known interfering gas may be used to compensate for the influential effects of the interfering gas on the measurement of the target gas. However, similar to the first sensor (i.e., the gas-sensitive material for the target gas), this second sensor may have a limited sensitivity. That is, the second sensor may also be affected by cross sensitivities. In addition, the second sensor may have a minimal effect where the level of the interfering signal exceeds the useful signal by a multiple.

Third, a filter may be used to suppress interference from interfering gases even where the interfering gases are permeable to a target gas. For example, an activated charcoal filter may remove an interfering gas. However, use of such a filter may prove problematic during long term operations. For example, the interfering gas may break through the filter when the limited capacity of the filter has been reached. In another example, where the sensor is operated at an elevated temperature, a catalytic filter may be used to transform an interfering gas, via a chemical reaction, into one or more non-interfering components (i.e., components that do not react with the gas-sensitive material to produce a signal). An example of a catalytic filter for decomposing alcohols is disclosed in German Patent No. DE 4310914, which is hereby incorporated by reference in its entirety. Although these catalytic filters may not exhibit the aforesaid filter capacity problems, they typically require temperatures above 300° C. Therefore, sensors using catalytic filters may not include structural elements with silicon (Si) chips that typically have a maximum operating temperature of about approximately 150° C.

SUMMARY OF THE INVENTION

According to one aspect of the invention, a FET gas sensor is configured to measure/detect a target gas in a gas mixture. The FET gas sensor has a gas channel for diffusion of a gas to be measured to a gas-sensitive layer that is in active connection with a field effect transistor for readout of a measurement signal, in which an electrochemical element is at least partially disposed within the gas channel to at least one of electrochemically convert interfering gases and activate a target gas, where the interfering gases are permeable to the target gas.

According to another aspect of the invention, an operating method is disclosed for the selective detection of a target gas in a gas mixture to be measured by a field effect transistor with a gas-sensitive layer disposed on a carrier substrate, wherein the gas mixture to be measured is prepared by an electrochemical element such that the measured gas mixture includes minimal amounts of interfering gases that interfere with the measurement of the target gas, and/or at least one target gas is activated such that it is detected by the gas-sensitive layer.

The disclosed FET gas sensors, in contrast to prior art FET gas sensors, includes a channel though which gas flows through to the detection area of the sensor. The sensor further includes a sensitive layer and an electrochemical element disposed in the channel and/or an air gap. The electrochemical element is adapted to decompose interfering gases by selective electrochemical conversion and thereby allow a target gas to pass through to a detection area.

In some embodiments, the gas channel for feeding the measurement gas into the sensor is made by lengthening the air gap between the channel insulation of the FET and the sensitive layer on a carrier substrate applied by hybrid technology. The electrochemical element includes at least two active electrodes to which a voltage is applied, at least one of which is in direct contact with the relevant measured gas mixture, and at least one of which is in contact with an active ion conductor at a typical operating temperature of the FET.

In other embodiments, the flow of gas into the sensor is regulated such that the electrochemical filter may adequately convert interfering gases into gases that are no longer detectable in the active sensor area (i.e., non-interfering gases).

In still other embodiments, when a proton conductor is used (e.g., a hydrogen ion conductor) in the electrochemical filter, both oxidizable and reducible interfering gases may be degraded in a comparable manner.

The disclosed FET gas sensor system has several advantages over prior art FET gas sensors. For example, the selectivity of a gas sensor system may be substantially increased by removing gases that lead to incorrect measurements (i.e., distort measurements of the target gas). In another example, in contrast to an ordinary filter (e.g., an activated charcoal filter), an electrochemical filter will not become consumed or saturated, which may permit more stable long-term continuous operation. Electrochemical filters are also typically smaller in structural shape than an ordinary filter. In still another example, in contrast to an ordinary filter, electrochemical filters are typically dynamic (i.e., they are not statically acting filters). For example, an electrochemical sensor may be self-monitored and self-calibrated via simple control of the dissociation voltage.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
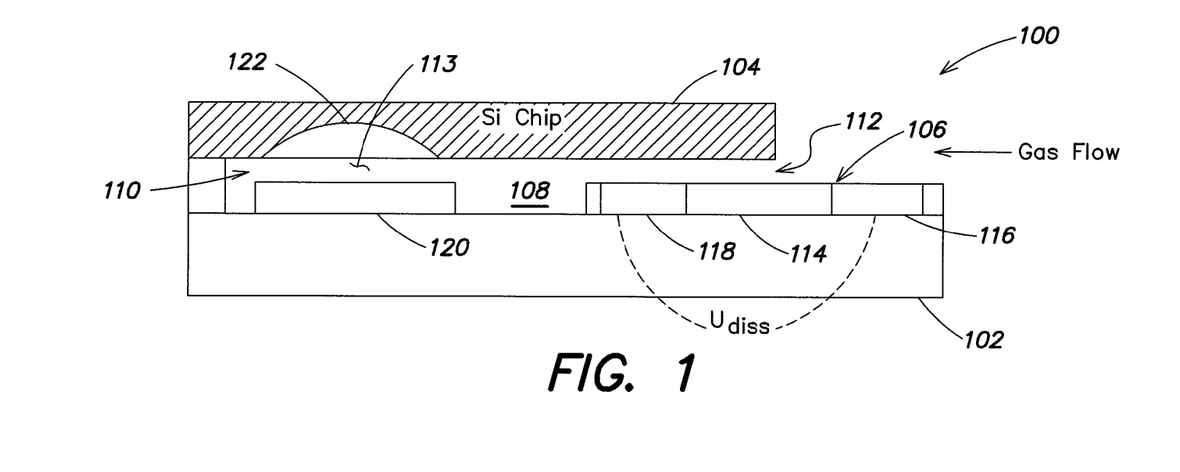
FIG. 1 illustrates one embodiment of an FET gas sensor system.

FIG. 1 illustrates one embodiment of an FET gas sensor system 100. The sensor 100 includes a carrier substrate 102, a chip 104 (e.g., a silicon chip), an electrochemical element/structure 106, a gas channel 108 (also referred to as a "gas diffusion channel"), and a detection area 110.

The carrier substrate 102 is constructed from any desired nonconductive material that allows, for example, only the preparation of the layers disposed on it. Suitable materials include, but are not limited to, ceramics (e.g., $Al_2O_3$, AlN, or $Si_3N_4$), glasses, or polymeric materials (e.g., conventional PCB materials like FR4 or the like).

The gas channel 108 includes an air inlet 112. The air inlet 112 is defined between the silicon chip 104 and the electrochemical element 106 such that entry of gas (or a gas mixture) and its diffusion to a sensor area/gas gap 113 (i.e., the region between the sensitive layer 120 and the transistor 122) is sharply limited. That is, the air inlet 112 thus the silicon chip 104 and the electrochemical element 106 is configured such that a small quantity of gas (or gas mixture) which enters the gas channel 108 may react with the electrochemical filter (i.e., the electrochemical element 106) and flows towards the sensor area/gas gap 113, where the small quantity of gas includes a quantity of target gas sufficient for detection.

The electrochemical element 106 includes an ion conductor 114, a first active electrode 116, and a second active electrode 118. The ion conductor 114 is disposed between and joins the first and the second electrodes 116, 118 on the carrier substrate 102. The first electrode 116 is configured outside of the gas channel 108. The second electrode 118 is configured in the gas channel 108. The first and the second electrodes 116, 118 are further adapted such that, for example, the second electrode 118 selectively converts interfering gas into one or more non-interfering components (e.g., a non-interfering gas), and the first electrode 116 provides a charge (e.g., a compensation charge) in the ion conductor 114, via a complementary reaction, that compensates for the conversion of the interfering gas into non-interfering components.

The ion conductor 114 is constructed from, for example, a material that conducts ions in a temperature range below 150° C. Examples of suitable materials include, but are not limited to, oxygen ion conductors (e.g., $LaF_3$) and hydrogen ion conductors (e.g., hydrogen uranyl phosphate tetrahydrate ($HUO_2PO_4 \cdot 4H_2O$), $NH_4TaWO_6$, NAFION, aluminum silicate+$Na_2O$ or $Li_2O$ or $K_2O$; ion-conducting sodium compounds such as Nasicon $Na_{1+x}Zr_2P_{3-x}Si_xO_{12}$, $Na_5YSi_4O_{12}$; or ion-conducting lithium compounds such as lithium nitride, lithium titanium phosphate).

The first and the second electrodes 116, 118 are constructed from, at least on their surfaces, a stable and catalytically active metal. Suitable metals include, but are not limited to, metals in the platinum group and their alloys (e.g., Pt, Pd, Pt/Rh, or silver).

The detection area 110 includes a sensitive layer 120 and a FET 122 (e.g., a CCFET or a SGFET). The sensitive layer 120 is disposed on the carrier substrate 102. The FET 122 is disposed in the silicon chip 104.

During operation of the sensor 100, gas or a mixture of gas flows/diffuses into the gas channel 108 through the air inlet 112. The mixture of gas is modified via the electrochemical element 106 (i.e., where an interfering gas is converted into one or more non-interfering components) such that a target gas that flows into the gas gap 113 (i.e., the region between the sensitive layer 120 and the FET 122) may be detected.

In one embodiment, the mixture of gas is modified via an oxidizing action induced by, depending on the polarity of the applied direct current ("d.c.") voltage "$U_{diss}$", one of the first and the second electrodes 116, 118 as the mixture flows through the gas channel 108, where the other electrode 118, 116 induces a reducing action. For example, where the second electrode 118 is configured as the oxidizing electrode, interfering gases that are more readily oxidizable than the target gas may be converted by oxidation into gases that no longer cause cross sensitivity (i.e., into non-interfering components). It should be noted that both the nature of the behavior of the electrodes and their oxidizing or reducing powers may be determined and controlled by the voltage $U_{diss}$.

Of course only oxidizable gases that are more easily oxidizable than the target gas may be removed by the procedure described. Similarly, the same applies to reducible gases.

Examples of common gases that may be removed by electrochemical reaction are shown in table 1 as follows:

TABLE 1

| Original gas | Converted to |
|---|---|
| Reduction of the gas by an electrode via a reducing action in the air gap | |
| $NO_2$ | NO |
| NO | $N_2$ |
| $O_3$ | $O_2$ |
| Oxidation of the gas by an electrode via an oxidizing action in the air gap | |
| HC (Hydrocarbons) | $H_2O$ and $CO_2$ |
| Alcohols, ketones, aldehydes | $H_2O$ and $CO_2$ |
| $H_2$ | $H_2O$ |
| $NH_3$ | $N_2$ and $H_2O$ |
| CO | $CO_2$ |

The electrochemical reaction of various gas components may be induced by an electrochemical filter (e.g., the electrochemical element 106) by selective application of a voltage of given polarity and magnitude thereto.

Depending on the polarity of the electrodes, this system may be used either for the degradative reaction of oxidizing gases or for the degradative reaction of reducing gases. The magnitude of the voltage to be applied in this case is typically between approximately 200 mV and 2 V.

When using an oxygen ion conductor, the FET gas sensor often detects gases with reducing action or $CO_2$. In this case, $NO_2$ with oxidizing action that often occurs at the same time in the application may lead to distinct interfering reactions in many FET gas sensors. However, the reactive $NO_2$ may be converted to the usually non-interfering NO according to the equation $$NO_2 + 2e^- \rightarrow NO + O^{2-}$$

by applying a negative voltage to the second electrode 118. The NO may also be decomposed with no residue by a stronger negative voltage:

$$2NO + 4e^- \rightarrow N_2 + 2O^{2-}$$

Gaseous oxygen is formed on the first electrode 116 as a counter reaction.

$$2O^{2-} - 4e^- \rightarrow O_2$$

With reversed polarity, unwanted reducible gases may be removed on the first electrode 116, for example according to the following equations:

$$2NH_3 + 3O^{2-} \rightarrow N_2 + 3H_2O + 6e^-, \text{ and}$$

$$2H_2 + 2O^{2-} \rightarrow 2H_2O + 4e^-.$$

As a counter reaction on the first electrode 116, the gaseous oxygen is taken up.

$$O_2 + 4e^- \rightarrow 2O^{2-}$$

By using a proton conductor (e.g., hydrogen ion conductor): (1) both oxidizable and reducible interfering gases may be degraded in a comparable manner; and/or (2) $NO_2$ is degraded on second electrode 118 in the presence of hydrogen or of another gas including hydrogen (e.g., $NH_3$, $CH_x$, etc.), for example by $$NO_2 + 2e^- + 2H^+ \rightarrow NO + H_2O.$$

As a counter reaction, gaseous hydrogen is taken up as a hydrogen ion in the proton conductor at the first electrode 116.

$$H_2 \rightarrow 2H^+ + 2e^-$$

The above reaction may of course be used directly to remove hydrogen where the electrodes wired in this way are in the gap. Similarly, $NH_3$ or hydrocarbon HC, for example, may be oxidized with an oxidizing connection of the first electrode 116.

$$2NH_3 \rightarrow N_2 + 6H^+ + 6e^-$$

$$6H^+ + 6e^- \rightarrow 3H_2$$

It should be noted that comparable mechanisms also apply to other ion conductors.

Figure 2:
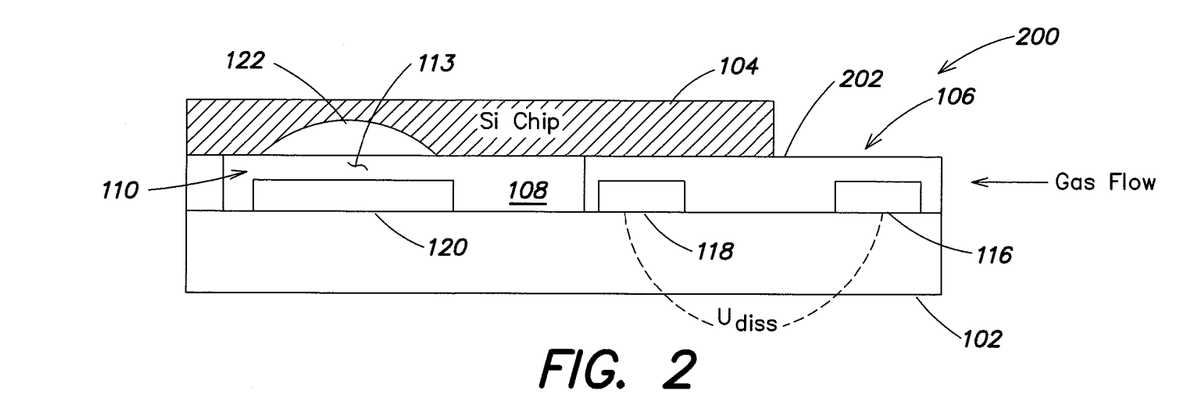
FIG. 2 illustrates another embodiment of a FET gas sensor system similar to the sensor in FIG. 1.

FIG. 2 illustrates another embodiment of a FET gas sensor system 200. As set forth above, it may be desirable to limit/reduce the gas infeed into the gas channel 108. By limiting the gas infeed to a reduced quantity, the electrochemical filter may, for example, completely remove/modify the interfering gases. Accordingly, an ion conductor 202 having an open pore structure fills up the entire gas diffusion channel 108 (i.e., completely extends between the carrier substrate 102 and the silicon chip 104). Thus, in contrast to the sensor 100 in FIG. 1 where gas flows into the gas channel 108 through the gas inlet 112, here, gas flows through an open-pore structure of the ion conductor 202. Similar to the sensor 100 in FIG. 1, the first electrode 116 is configured outside of the gas channel 108, whereas the second electrode 118 is configured in the gas channel 108.

Figure 3:
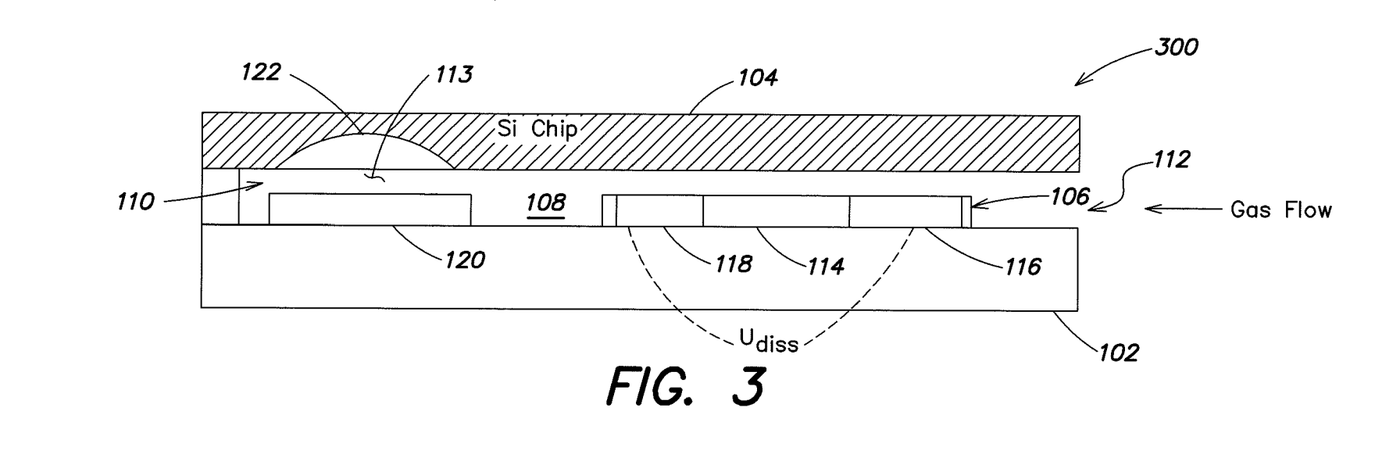
FIG. 3 illustrates another embodiment of a FET gas sensor system similar to the sensor in FIG. 1.

FIG. 3 illustrates another embodiment of a FET gas sensor system 300. As illustrated, both the first and the second electrodes 116, 118 are configured in the narrow gas diffusion channel 108. As a result, both reducing and oxidizing gases are decomposed by the electrochemical filter 106. The decomposition thresholds may be set via the applied potential $U_{diss}$. Such an arrangement is particularly suitable for selectively detecting inert gases like $CO_2$, for example, that are unchanged by the filter, with respect to their redox behavior.

Figure 4:
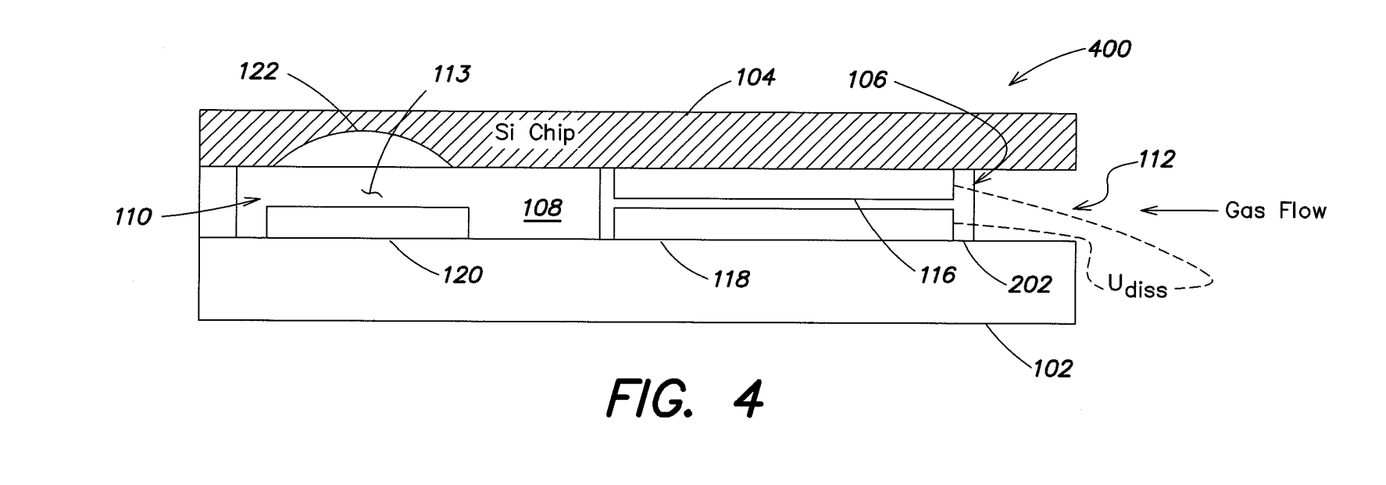
FIG. 4 illustrates another embodiment of a FET gas sensor system which combines the sensors in FIGS. 2 and 3.

FIG. 4 illustrates another embodiment of a FET gas sensor system 400 which combines the characteristics of the sensors 200, 300 in FIGS. 2 and 3. As illustrated, two electrodes 116, 118 are diametrically configured within the gas channel 108 such that one is disposed on the carrier substrate 102 and the other is disposed on the silicon chip 104. Each electrode 116, 118 is further configured having a relatively large surface area such that an exchange between the gas and a surface of each electrode 116, 118 may be improved. The porous ion conductor 202 extends between and around the two electrodes 116, 118 filling the gas channel 108.

Figure 5:
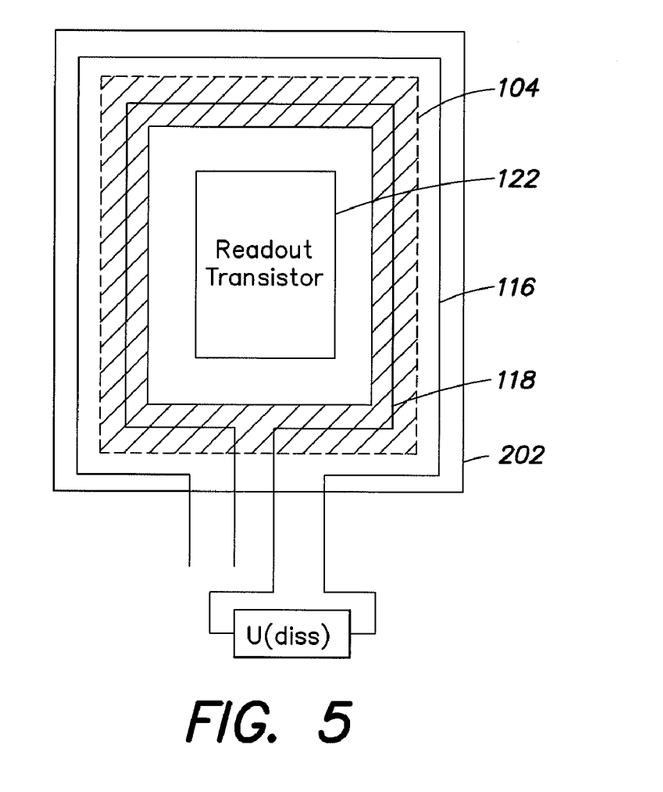
FIG. 5 illustrates one embodiment of the first and second electrodes included in the sensor in FIG. 4.

FIG. 5 illustrates one embodiment of the first and the second electrodes 116, 118 of FIG. 4 configured as annular structures. This configuration allows for a substantially larger gas inlet than a structure closed on one side, and thus the gas exchange and the response time of the sensor is improved.

The disclosed electrochemical filters may be self-monitored and self-calibrated. For example, the gas infeed may be selectively filtered and varied by regulating (e.g., by increasing or decreasing) the control voltage $U_{diss}$ applied to the electrodes 116, 118. In another example, multiple gases may be sequentially measured by continuously increasing the filtering of the electrochemical filter. In still another example, baseline variations of the sensor may be efficiently reduced by removing the target gas from the detection area, via the electrochemical filter, by modulation of the control voltage $U_{diss}$, and providing an artificial zero point.

In some embodiments, the target gas may be activated by the electrochemical filter. For example, an undetectable gas may be converted into a gas to which the gas-sensitive material reacts by modifying it in the electrochemical filter as set forth above.

In alternate embodiments, a FET gas sensor may include a multistage electrochemical filter (not shown). The multistage electrochemical filter includes a plurality of first and second electrodes in the gas channel. Each electrode may be constructed from different materials and/or be operated at different voltages.

Although the present invention has been illustrated and described with respect to several preferred embodiments thereof, various changes, omissions and additions to the form and detail thereof, may be made therein, without departing from the spirit and scope of the invention.

What is claimed is:

1. A FET gas sensor having a gas channel for diffusion of a gas to be measured to a gas-sensitive layer that is in active connection with a field effect transistor for readout of a measurement signal, in which an electrochemical element is at least partially located within the gas channel to at least one of electrochemically convert interfering gases and activate a target gas, where the interfering gases are permeable to the target gas.

2. The gas sensor of claim 1, where the gas channel has an air gap that extends between channel insulation of the FET and the gas-sensitive layer.

3. The gas sensor of claim 1, where the electrochemical element is positioned in and partially fills a cross section of the gas channel.

4. The gas sensor of claim 1, where the electrochemical element includes a porous material and is positioned in and fills a cross section of the gas channel.

5. The gas sensor of claim 1, where the electrochemical element comprises an ion conductor and at least two active electrodes which receive an external voltage, where the ion conductor is positioned between and joins the two electrodes, and where at least one of the electrodes is in contact with the gas to be measured.

6. The gas sensor of claim 5, where
one electrode is positioned in the gas channel to convert the interfering gases; and
the other electrode is positioned outside the gas channel to provide a complementary reaction for charge compensation in the ion conductor.

7. The gas sensor of claim 5, where the ion conductor comprises a material capable of withstanding temperatures up to approximately 150° C.

8. The gas sensor of claim 5, where each electrodes comprises, at least on a surface thereof, a mechanically stable and catalytically active metal.

9. The gas sensor of claim 5, where the ion conductor is a proton conductor.

10. The gas of claim 1, where the electrochemical element has a multistage design.

11. A method for the selective detection of a target gas in a gas mixture to be measured by a field effect transistor with a gas-sensitive layer disposed on a carrier substrate, wherein the gas mixture to be measured is prepared by an electrochemical element such that the measured gas mixture includes minimal amounts of interfering gases that interfere with the measurement of the target gas, and/or at least one target gas is activated such that it is detected by the gas-sensitive layer.

12. The method of claim 11, where the electrochemical element comprises a plurality of electrodes and an external voltage is applied to the electrodes such that one of the electrodes has oxidizing action and the other electrode has a reducing action, where one of the electrodes chosen for reducing interfering gases is positioned in a gas channel.

13. The method of according to claim 12, where potential of the external voltage is varied to match dissociation or decomposition thresholds for given gases in the gas mixture.

14. The method to claim 12, where filtering action of the electrochemical filter element is selectively controlled by regulating the external voltage for the self-monitoring or self-calibration of the electrochemical element.

15. The method of claim 14, where the target gas is electrochemically converted by the electrochemical element.

16. A FET gas sensor for detecting a target gas in a gas mixture, where the gas mixture includes at least one of an interfering non-target gas and an unknown target gas, the sensor comprising:
a gas channel having an inlet, the gas channel extending between a carrier substrate and a silicon chip;
an electrochemical element disposed at least partially in the gas channel proximate the inlet, which electrochemical element at least one of decomposes the interfering non-target gas and activates the unknown target gas to provide a modified gas mixture; and
a target gas detector including an field effect transistor and a gas-sensitive layer defining a gas gap therebetween, which target gas detector is disposed in the gas channel and detects the target gas in the modified gas mixture.

17. The sensor of claim 16, where the electrochemical element comprises an ion conductor positioned between and connected to first and second active electrodes, and where the electrodes each receive a control voltage.

18. The sensor of claim 17, further comprising a power source that selectively provides the control voltage to the electrodes.

19. The sensor of claim 17, where
the first electrode is disposed outside of the gas channel; and
the second electrode is disposed in the gas channel.

20. The sensor of claim 17, where both the first and the second electrodes are disposed in the gas channel.

21. The sensor of claim 20, where the first electrode is disposed on the carrier substrate and the second electrode is diametrically disposed on the silicon chip.

22. The sensor of claim 17, where the electrochemical element extends between the carrier substrate and the silicon chip in the gas channel.

23. The sensor of claim 22, where the ion conductor has a porous structure that permits gas flow from the inlet, through the gas channel, to the target gas detector.

24. The sensor of claim 16, where the electrochemical element partially extends between the carrier substrate and the silicon chip in the gas channel.

25. A method for detecting a target gas in a gas mixture, where the gas mixture includes at least one of an interfering non-target gas and a unknown target gas, the method comprising:
providing a FET gas sensor comprising an inlet between a carrier substrate and a silicon chip, an electrochemical element and a target gas detector;
receiving the gas mixture via the inlet;
modifying the gas mixture via the electrochemical element by at least one of decomposing the interfering non-target gas into a non-interfering component and activating the unknown target gas to provide the target gas; and
detecting the target gas in the modified gas mixture via the target gas detector.

26. The method of claim 25, further comprising at least one of self-monitoring and self-calibrating the electrochemical element.

27. The method of claim 25, where the electrochemical element comprises an ion conductor disposed between and connected to first and second active electrodes, and where each of the electrodes receive a control voltage.

28. The method of claim 27, further comprising controlling the electrochemical element by selectively providing the control voltage to the electrodes.

* * * * *

UNITED STATES PATENT AND TRADEMARK OFFICE
CERTIFICATE OF CORRECTION

PATENT NO. : 7,707,869 B2  Page 1 of 1
APPLICATION NO. : 11/587172
DATED : May 4, 2010
INVENTOR(S) : Fleischer et al.

It is certified that error appears in the above-identified patent and that said Letters Patent is hereby corrected as shown below:

Column 1
Line 37, delete "uncontacted gate 98" and insert --uncontacted gate 28--
Line 37, delete "electrode 10" and insert --electrode 30--

Column 7
Line 46, Claim 8 delete "electrodes" and insert --electrode--
Line 51, Claim 10 after "gas" insert --sensor--

Column 8
Line 1, Claim 13 delete "according to"
Line 4, Claim 13 delete "method to" and insert --method of--
Line 4, Claim 14 before "filtering" insert --a--
Line 5, Claim 14 delete "filter"

Signed and Sealed this

Fifteenth Day of June, 2010

David J. Kappos
*Director of the United States Patent and Trademark Office*